United States Patent [19]

Man

[11] Patent Number: 4,706,689
[45] Date of Patent: Nov. 17, 1987

[54] IMPLANTABLE HOMING DEVICE

[76] Inventor: Daniel Man, 851 Meadows Rd., Suite 222, Boca Raton, Fla. 33432

[21] Appl. No.: 4,753

[22] Filed: Jan. 8, 1987

Related U.S. Application Data

[63] Continuation of Ser. No. 792,935, Oct. 30, 1985, abandoned.

[51] Int. Cl.[4] ............................................. A61B 5/00
[52] U.S. Cl. .................................... 128/903; 340/539
[58] Field of Search ............... 128/1 R, 903, 904; 340/539

[56] References Cited

U.S. PATENT DOCUMENTS

| | | | |
|---|---|---|---|
| 3,639,907 | 2/1972 | Greathatch | 128/903 |
| 3,662,758 | 5/1972 | Glover | 128/903 |
| 3,724,455 | 4/1973 | Unger | 128/903 |
| 3,852,713 | 2/1974 | Roberts et al. | 340/539 X |
| 3,898,984 | 8/1975 | Mandel et al. | 128/903 |
| 3,918,034 | 11/1975 | Orth | 340/539 |
| 4,220,156 | 9/1980 | Schulman et al. | 128/903 |
| 4,223,678 | 9/1980 | Langer et al. | 128/903 |
| 4,237,900 | 12/1980 | Schulman et al. | 128/903 |
| 4,281,664 | 8/1981 | Duggan | 128/903 |
| 4,401,872 | 7/1978 | Pappas | 340/539 |
| 4,441,210 | 4/1984 | Hochmair et al. | 128/903 |

FOREIGN PATENT DOCUMENTS

| | | | |
|---|---|---|---|
| 2386875 | 11/1978 | France | 128/903 |
| 2420333 | 10/1979 | France | 128/903 |

*Primary Examiner*—Edward M. Coven
*Attorney, Agent, or Firm*—Alfred E. Miller

[57] ABSTRACT

A new apparatus for location and monitoring of humans has been developed. The device employs a unique programmable signal generator and detection system to locate and monitor the movement of individuals. It additionally utilizes a physiological monitoring system to signal a warning for the necessity for immediate help. The device is small enough to be implanted in young children as well as adults. The power supply and signal generator are designed to function at a low duty cycle for prolonged periods before recharging.

16 Claims, 4 Drawing Figures

IMPLANTABLE HOMING DEVICE

This application is a continuation, of application Ser. No. 792,935, filed 10/30/85, now abandoned.

BACKGROUND OF THE INVENTION

1. Field of the Invention

This invention relates to a system of monitoring and locating humans and more particularly to a homing device which is small enough to implant under the skin of a human.

2. Description of Prior Art

This implantable homing device meets a growing need in the community for monitoring and locating individuals. The three areas where this device should make the greatest impact are (1) the prevention of kidnapping and/or facilitating the recovery of the kidnapped victim; (2) the relief of overcrowded prison conditions by providing an easy means to enforce house or area arrest; and (3) the monitoring of outpatients or nursing home patients in order to decrease medical care costs.

Kidnap Victims

Much suffering and anxiety will be readily avoided by implanting the homing device in potential kidnap victims. The monitoring of these potential victims will permit the rapid deployment of law enforcement personnel to quickly recover the victim and capture the perpetrators.

Modified Confinement

With overcrowded conditions and the expense of building new prisons has come the realization that other modes of confinement or limitation may meet society's needs. The implantable homing device can be utilized to enforce house arrest or limit movements of parolees. The system can monitor the individual with the implanted device, and trace his whereabouts. The receiving system computer can easily track the movements of the individual under surveillance and warn the appropriate authorities to intervene.

Outpatient Monitoring

The trend to decrease hospital costs by releasing patients early is facilitiated with the implantable homing device. Physiological probes are utilized to monitor the medical condition of the patients. Whenever the physiological parameter reached a preset threshold the appropriate medical personnel could be alerted and medical care dispatched. This procedure has the advantage of decreasing medical costs and allowing the recovery from health problems to occur in the friendly, familiar surroundings of home. Furthermore, it can be used to monitor long-term care patients such as those with Alzheimer disease.

Various attempts have been made to monitor or locate animate and inanimate objects. Two devices, described in U.S. Pat. No. 4,262,632 issued to J. P. Hanton et al. on Apr. 21, 1981, and U.S. Pat. No. 3,034,356 which was issued to W. J. Bieganski et al. on May 15, 1962, employ capsules which are swallowed and transmit signals from the gastrointestinal tract. Both of these devices have a very limited range and are not useable for monitoring purposes. The Hanton et al. system was designed for livestock identification at a range of less than 20 feet. The Bieganski et al. device was again designed for short distance monitoring of gastrointestinal pressure. The construction and frequencies utilized in these devices are not suitable for the purposes of the present invention.

U.S. Pat. No. 3,618,059 which was issued to M. F. Allen on Nov. 2, 1971, employs a device to locate personal property and packages. The device is designed to be activated by the unwanted movement of the object. This device, although valuable for tracking purposes, is not small enough for human implantation or for physiological monitoring.

Various other devices have been developed for tracking and locating purposes. U.S. Pat. No. 3,806,936 which issued to C. A. Koster on Apr. 23, 1974, discloses a personal locator which can be attached to the clothing of an individual and activated when the person is lost. The device in U.S. Pat. No. 3,790,948 which issued to J. M. Ratkovich on June 12, 1972, is designed to follow wild game which has been shot by a hunting arrow containing a radio transmitter. U.S. Pat. No. 3,782,730 which issued to S. A. Horchler on Jan. 1, 1974, shows a device having a transmission means embedded in a golf ball to find lost balls.

These devices were designed for short term monitoring and activation when needed. They are incompatible with continuous long term monitoring and locating. They also employ devices which are much too large for utilization in implantation. The implantation aspect of the invention supplies a device which can be concealed from other individuals, not readily destroyed or lost and adapted for physiological monitoring. All of these aims are necessary to meet the growing needs of this device. The small size, low upkeep and high stability make it an ideal device for monitoring and locating children or adults, sick or healthy and in law enforcement.

SUMMARY OF THE INVENTION

The present invention provides a new means for locating and monitoring humans. Its utilization will decrease the fears and anxiety of parents whose children are more likely to be kidnapped and of diplomats at risk. This will lead to significant economic benefits in both the law enforcement and health care industries.

The locating and monitoring means are designed to be implanted under the skin behind the ear. Its small size and hidden, elevated location in the body make it an ideal transmitter system. The device is encapsulated in a high impact, hermetically sealed container which is subcutaneously or subperiostealy implanted. It may have protruding probes through a gromet structure in the skin. This device emits a signal in the range of the cellular telephone system and/or satellite communication system. A series of detection locations monitors the signal and locates the individual by triangulation. Continuous monitoring by computer locates and traces the movement of the individuals.

The device is composed of a power supply which is designed for long term use. Although not essential, this power supply is rechargeable. The signal generator is programmable and operates on a low duty cycle. This operation utilizes very little energy thus prolonging the life of the power source. The programmable function allows each subscriber to generate a unique signal, as well as, to generate a distress signal for emergency conditions.

A further advancement of the device is the incorporation of a physiological monitoring system. This system is programed with threshold valves for the physiological parameters monitored. These physiological parameters can be either physical (for example, heat, blood pressure), and/or chemical (for example pH, metabolities). The monitoring system has one or more probes to measure the physical or chemical changes in the body. Whenever an individual's body changes, resulting in values above or below the threshold, whichever is appropriate, the distress signal is activated. This distress signal can also be manually activated.

The size of the device is such that it can be implanted in a variety of individuals from young children to adults, enabling a wide utilization of the device. An object of this invention is the monitoring of individuals at risk for being kidnapped. Additionally, this device will aid law enforcement agencies in monitoring house arrest and/or parole. Further utilization is in the monitoring of the recovery of outpatients so that they spend less time in the hospital or in nursing homes, such as patients suffering from Alzheimer disease.

Those skilled in the art will recognize the above described features and superior aspects of the present invention as well as other and further objects features and advantages that will be apparent from the following description of presently preferred embodiments of the invention given for the purpose of disclosure.

BRIEF DESCRIPTION OF THE DRAWINGS

So that the manner in which the above-featured advantages and objects of my invention will be more readily understood, a more particular description of the construction and operation may be had by reading the following specifications and by reference to the accompanying drawings, forming a part thereof.

DESCRIPTION OF PREFERRED EMBODIMENT

In the description which follows the drawings are shown in schematic form in the interest of clarity and conciseness. It will be readily apparent to one skilled in the art that various substitutes and modifications may be made to the invention disclosed herein without departing from the scope and spirit of the invention.

Figure 1:
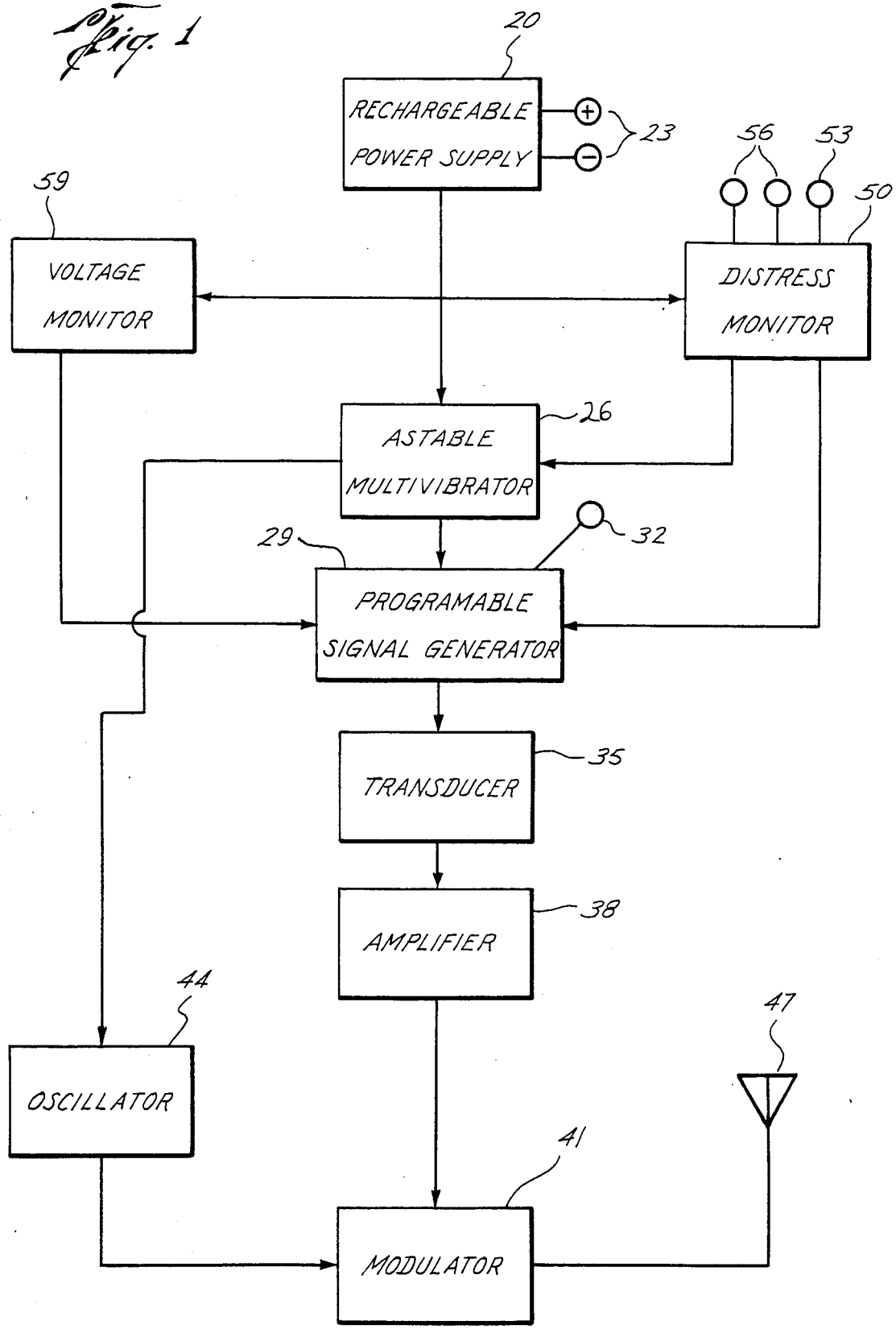
FIG. 1 is a block diagram of the electronic components encapsulated in the housing element of the present invention.

Referring to the schematics in FIG. 1. The power supply 20 can be either fixed or rechargeable. Silver oxide or lithium oxide batteries are employed for fixed power supplies 20. The silver or lithium batteries have a very long shelf life, a capacity for high current/short duration current bursts, a high power capacity per size, and a high cell voltage which allows them to power complementary metal-oxide-semiconductor (CMOS) integrated circuits. These characteristics combined with the batteries intoxicity, small size, resistance to human body conditions and flat discharge capacity satisfy the power requirements of the implantable homing device.

Figure 4:
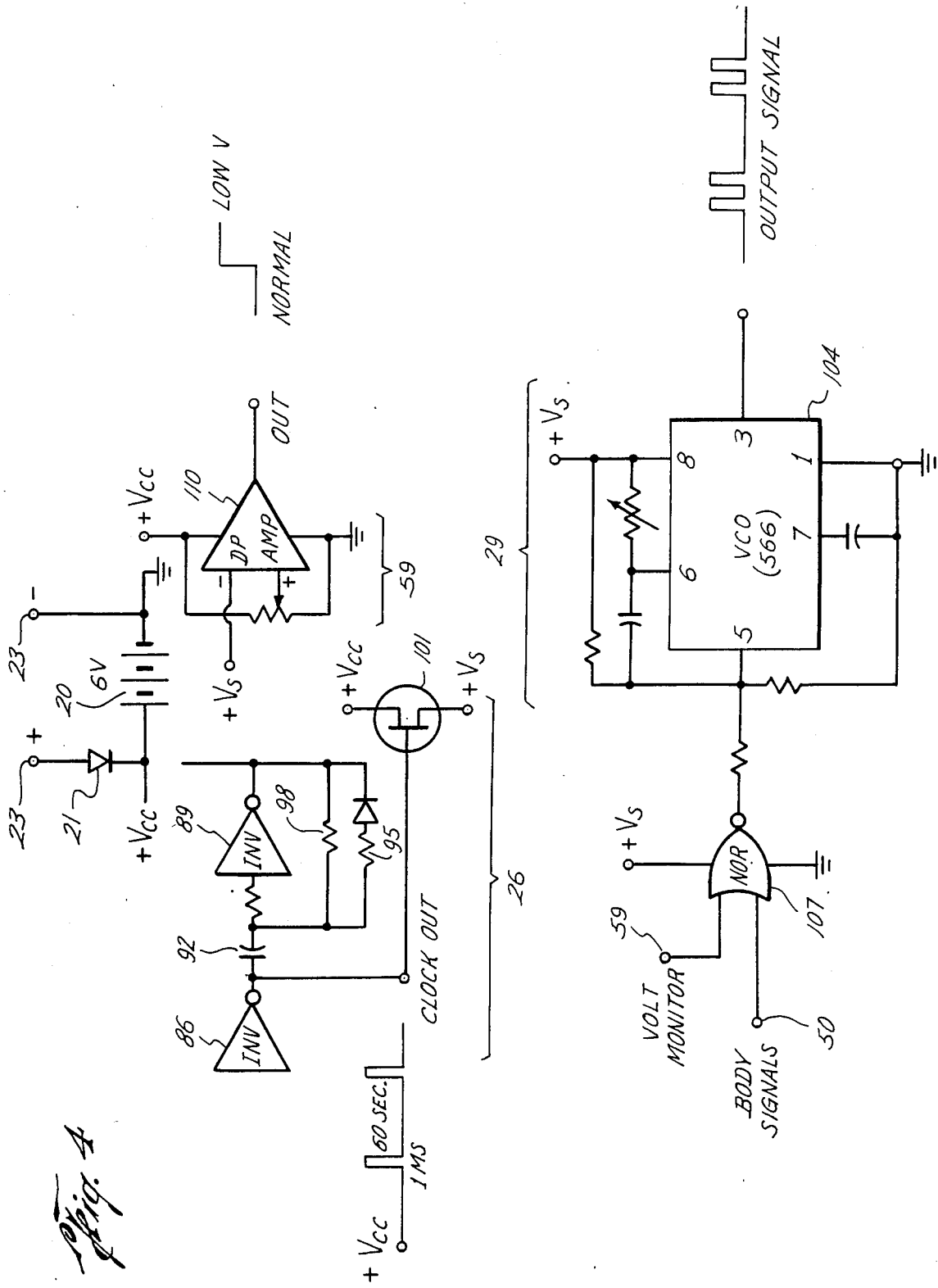
FIG. 4 is a detailed schematic of the electronics for the astable multivibrator and the programmable signal generator.

The rechargeable power supply 20 utilizes contact probes 23 to the external environment for recharging purposes. These contact probes 23 easily connect to a charging unit (not shown) for periodic recharging. Because of the previously described characteristics and its rechargeability, the present embodiment employs a silver oxide battery of 6 v for the rechargeable power supply 20. The power supply is coupled in series with a diode 21 FIG. 4 to prevent accidental discharge.

The power supply 20 provides energy to the astable multivibrator 26, which is necessary for the successful operation of the implantable homing device. The astable multivibrator 26 operates the remaining circuits on a very low duty cycle thus prolonging the life of the power supply 20. The astable multivibrator circuit FIG. 4 uses two CMOS inverters 86 and 89 connected as a self-regenerating clock. This mode of operation is clear to anyone familiar with digital circuiting. The frequency generated by this circuit is governed by the equation $F = 1/[R2*C + (R1*R2/R1 + R2*C]$ where F is frequency, C is capacitance and R1 and R2 are resistors. By way of example and not limitation, a capicitance of 3 $\mu$F a R1, 95, of 18M$\Omega$ and a R2, 98, of 3K$\Omega$ will produce a 1 milisecond positive spike and 60 seconds of 0 voltage. This output is fed to a VMOS or PNP transistor acting as a main power switch 101, which feeds the main circuit with the proper duty cycle voltage. By way of further example and not limitation, the capacitance and resistors can be changed such that this low duty cycle needs full power only 1 millisecond per 5 minutes. During the remainder of the cycle, negligible power is needed to maintain the multivibrator itself.

The programable signal generator 29 is necessary to provide each human subscriber with a unique tonal signature. This subscriber is the guardian of or individual in whom the device has been implanted. It is based on a CMOS 566 integrated circuit 104 configured as a voltage controlled oscillator in a frequency shift keying (FSK) mode. The circuit is governed by the equation $$F_c = 2*(V_s - V_i)/R1*C1*V_s$$

where $F_c$ is the center frequency, $V_s$ is the supply voltage, $V_i$ is the voltage at pin 5 and R1 is the resistance at the potentiometer of pin 8. A multi input NOR gate 107 is used to clock the different frequency outputs. The NOR gate 107 monitors all inputs such as body signals and voltage. Any signal which changes the logical state from a normal low to an alert high will cause the output of the NOR gate 107 to invert, and shift the output frequency of the variable controlled oscillator 104. This device can be preprogramed before implantation or have an external program probe 32 for reprograming after implantation.

The tonal signal is passed through a standard transmission circuit comprising a transducer 35, amplifier 38 and a modulator 41. The astable multivibrator through the oscillator 44 sends the frequency to the modulator 41. The unique signature is then sent out in a selected frequency range. This frequency range can be either in the cellular, microwave, radio or satellite transmission ranges.

This unique signature, by way of illustration and not limitation, could be sent out in the frequency range of 806 to 960 mHz, which is the current frequency range in the cellular system. The unique signature is sent to the antenna 47 which has been miniaturized and designed to provide maximum transmission effeciencies. Those skilled in the art will readily realize that the device can also operate in any expanded frequency range.

As a further illustration and by no means limitation, the IHD can also operate in an expanded communications satellite system. Satellite systems already exist which receive in international radio frequencies for distress signals. Because of their ranges, communication satellites have an advantage over their main competitors, the microwave system and the coaxial cable system. Today's satellites are equipped with sophisticated antennae and advanced electronic equipment that are necessary to provide clear and strong signals. Furthermore, communication satellites are placed in geostationary orbit directly above the equator at altitudes of 22,300 miles. Because of the apparent immobility, antennae can be permanently pointed at the satellite ready to beam and receive messages at any time. The IHD can be used to beam a signal either to the cellular system or through a local cable television system which will then transmit it to the communication satellite and back to earth. Those individuals interested in a short distance control of the IHD will subscribe to the cellular system, while persons who are interested in having complete control over the IHD carrier will subscribe to the satellite communication program. The satellite communication program will allow monitoring of individuals worldwide. The IHD, as currently configured, will work in either of the described examples of transmission frequency.

Although not necessary for the functioning of the homing device, an improved and expanded distress monitor system 50 expands the capabilities of the device. This system when activated sends signals to both the astable multivibrator 26 and the programable signal generator 29 to send a unique signal indicating the need for immediate contact. This signal is both transmitted at a higher duty cycle mode, allowing more frequent information density for monitoring, and triggers the signal generator to change from normal tone to emergency tone. The distress monitor is designed to be activated either by a manual control switch 53 or through at least one physiological probe 56. The manual control switch 53 is an on-off toggle switch which the subscriber physically activates. The physiological probes 56 are also designed to function in a binary mode. Functioning in an on-off mode simplifies the necessary electronics. A preset threshold value is programed into the distress signal for each physiological parameter. When the subscribers physiological measurement exceeds the threshold value, the distress monitor system 50 is activated. One in the art will recognize that this threshold can be either a minimum or maximum value. Not as a limitation but for example only, this invention can operate using blood pressure sensors, heart rate sensors, and respiratory sensors. Hence, the physiological parameters of patients who have been discharged from the hospital can be monitored from a central location which could dispatch the necessary medical help. Thus, the hospital costs for patients can be reduced by changing their status from in-patient to out-patient. Alzheimer and other long-term care patients can be similarly monitored.

A further improvement comprises the addition of a voltage monitor 59 to the signal generator 29 to provide transmission of a special low power signal. The voltage monitor 59 uses a classical inverting operational amplifier 110 as a comparator. The positive input gate is connected to a constant voltage reference and the negative input gate to the supply voltage. In this mode of operation the output will remain in a logical low as long as the supply voltage remains above the reference voltage. It will change to a logical high when the supply voltage drops to the pre-determined alarm point. The operational amplifier 110 is a single voltage micro power type. The monitoring station then senses the low power signal and contacts the subscriber to remedy this problem.

Figure 2:
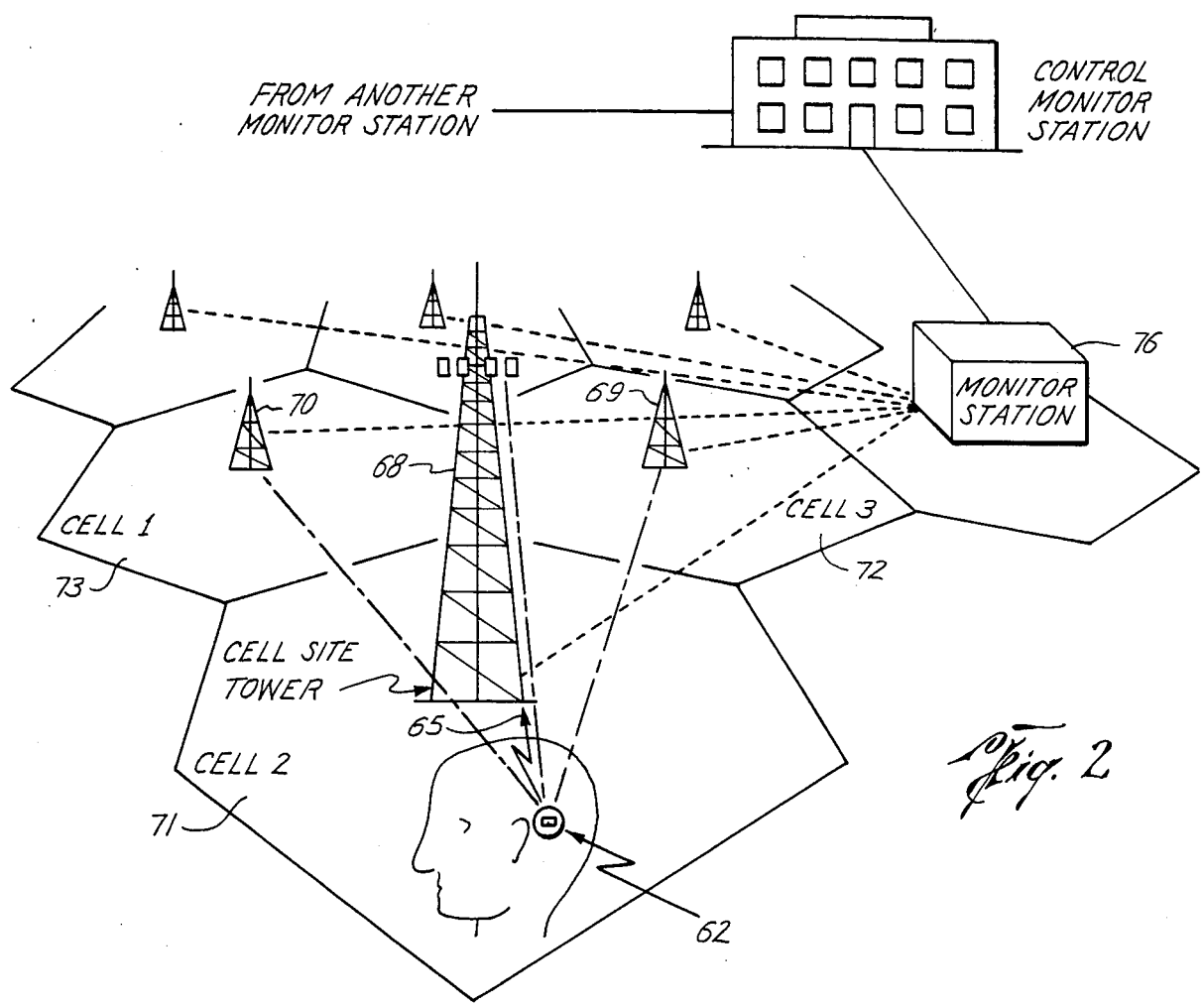
FIG. 2 illustrates an embodiment of the system of the present invention.

In FIG. 2 is a schematic of the method utilized to detect and locate the subscriber. The implantable homing device 62 located under the skin behind the ear sends out a transmission pulse 65 which is constantly monitored by at least 3 towers 68, 69 and 70 in different cells 71, 72 and 73. Since the coordinates of the three towers are known, the subscriber can be located by well known triangulation means with little error. All of the calculations and locations can be done by a computer at the monitoring station 76. A succession of points gathered in this manner can be plotted to trace the subscriber's movements, a very helpful technique in locating the kidnap victims or monitoring the parole or house arrest of individuals. Furthermore, as an individual passes from one cell to another, the monitoring can likewise be shifted from one tower to another as is already the mode of operation in the cellular phone network.

Figure 3:
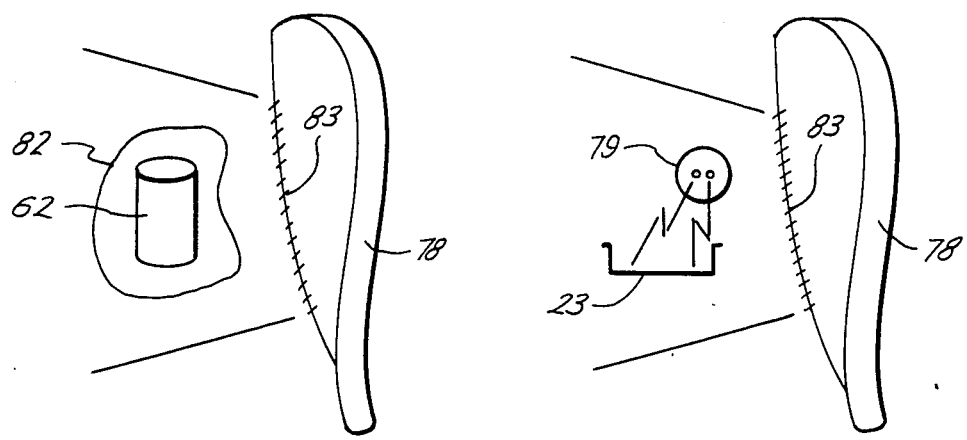
FIG. 3 illustrates the implantation methods employed for the homing device.

FIG. 3 shows a schematic of two embodiments of the invention implanted behind the ear 78. The implantable homing device 62 can be completely under the skin with no external probes as can be seen when a skin flap 82 is removed. It can also be partially under the skin where a grommet 79 arrangement allows the implantable homing device 62 to connect with the external environment through a plurality of probes 23. In either case a simple incision 83 is made in the post auricular sulcus. One versed in the art will recognize the similarity to the methods of implantation employed in hearing devices.

The design described herein used off-the-shelf state of the art integrated circuits. The device during mass production can be packed into a single CMOS large-scale integrated (LSI) circuit. This will significantly improve space utilization, energy consumption and reliability.

One skilled in the art will readily appreciate that the present invention is well adapted to carry out the objects and attain the ends and advantages mentioned as well as those inherent therein. The structure and techniques described herein and depicted in the accompanying drawings, while presently representing the preferred embodiments are only intended to be exemplary and are not intended as limitations on the scope or design of the invention.

What is claimed is:

1. In an implantable homing device having a transmitter, and a source of power connected to apply operating current to said transmitter; the improvement wherein said source of power comprises oscillator means, a battery connected to energize said oscillator means, means applying the output of said oscillator means to said transmitter as a source of operating current therefor, whereby said transmitter is intermittently operated, said transmitter comprising an oscillator and a programmable signal generator connected to provide a programmable output coded signal for modulating said oscillator, and means responsive to the voltage of said battery for controlling said programmable generator, whereby the output of said transmitter is modulated as a function of the voltage of said battery.

2. The implantable homing device of claim 1 further comprising contact means connected to said battery to enable the external recharging thereof.

3. The implantable homing device of claim 1 wherein said oscillator means comprises a multivibrator.

4. The implatable homing device of claim 3 wherein said multivibrator comprises an astable multivibrator, and further comprising a transistor connected to apply the output of said multivibrator to said transmitter as the operating supply thereof.

5. The implantable homing device of claim 4 wherein said multivibrator has a duty cycle to supply operating current to said transmitter of no more than 1 millisecond in 5 minutes.

6. The implantable homing device of claim 1 wherein said generator is a voltage controlled oscillator and includes means for varying the output thereof in accordance with a determined code, whereby signals output from said transmitter may uniquely identify said device.

7. The implantable homing device of claim 6 wherein said voltage controlled oscillator is connected to operate in an FSK mode, and further comprising means for clocking the different frequency outputs of said oscillator.

8. The implantable homing device of claim 7 wherein said clocking means is connected to control the output of said oscillator in accordance with a determined program.

9. The implantable homing device of claim 6 further comprising monitor means connected to modify the output of said oscillator, whereby output signals of said device are modulated in accordance with the output of said monitor means.

10. The implantable homing device of claim 1 wherein said oscillator means comprises an astable multivibrator connected to have a duty cycle of no greater than 1 millisecond in one minute.

11. The implantable homing device of claim 1 wherein said oscillator means comprises an astable multivibrator and said transmitter comprises an oscillator, a programmable signal generator, and modulator means connected to modulate the output of said oscillator with the output of said signal generator, said signal generator comprising means for producing a signal having a frequency that varies in a predetermined manner.

12. The implantable homing device of claim 11 further comprising monitor means connected to said signal generator for modifying said predetermined manner of variation of said output of said generator.

13. The implantable homing device of claim 11 further comprising monitor means connected to said oscillator means for modifying the duty cycle thereof.

14. The implantable homing device of claim 11 further comprising monitor means connected to sense the voltage of said battery and to modify the output of said transmitter in response to a low battery voltage condition.

15. In an implantable homing device having a tranmitter, and a source of power connected to apply operating current to said transmitter; the improvement wherein said source of power comprises oscillator means, a battery connected to energize said oscillator means, means applying the output of said oscillator means to said transmitter as a source of operating current therefor, whereby said transmitter is intermittently operated, said transmitter comprising an oscillator and a programmable signal generator connected to provide a programmable output coded signal for modulating said oscillator, monitor means connected to said programmable signal generator and responsive to determined stimulus, whereby said transmitter is modulated as a function of said stimulus, and means coupling said monitor means to said oscillator means for controlling the frequency of oscillation thereof, whereby the rate of output of said device is varied in response to said stimulus.

16. The implantable homing device of claim 15 further comprising means responsive to a determined stimulus and connected to said oscillator means for increasing the duty cycle of said oscillator means, whereby the rate of output of said device is increased in response to said stimulus.

* * * * *